United States Patent [19]

Berg

[11] Patent Number: 5,417,813
[45] Date of Patent: May 23, 1995

[54] SEPARATION OF 1-BUTANOL FROM 2-PENTANOL BY AZEOTROPIC DISTILLATION

[75] Inventor: Lloyd Berg, 1314 S. Third Ave., Bozeman, Mont. 59715

[73] Assignee: Lloyd Berg, Bozeman, Mont.

[21] Appl. No.: 272,805

[22] Filed: Jul. 11, 1994

[51] Int. Cl.⁶ .......................... B01D 3/36; C07C 29/82
[52] U.S. Cl. ........................................ 203/60; 203/62; 203/68; 203/69; 203/70; 568/913
[58] Field of Search ...................... 203/68, 69, 70, 60, 203/62; 568/913

[56] References Cited

U.S. PATENT DOCUMENTS

| | | | |
|---|---|---|---|
| 2,483,246 | 9/1949 | Stribley | 203/60 |
| 2,500,329 | 3/1950 | Steitz | 203/69 |
| 2,552,911 | 5/1951 | Steitz | 203/69 |
| 2,575,243 | 11/1951 | Carlson et al | 203/60 |
| 2,575,285 | 11/1951 | Carlson et al. | 203/63 |

*Primary Examiner*—Wilbur Bascomb, Jr.

[57] ABSTRACT

1-Butanol is difficult to semarate from 2-pentanol by conventional distillation or rectification because of the proximity of their boiling points. 1-Butanol can be readily separated from 2-pentanol by azeotropic distillation. Effective agents are 1-octene, hexane and methyl cyclohexane.

1 Claim, No Drawings

SEPARATION OF 1-BUTANOL FROM 2-PENTANOL BY AZEOTROPIC DISTILLATION

FIELD OF THE INVENTION

This invention relates to a method for separating 1-butanol from 2-pentanol using certain organic liquids as the agent in azeotropic distillation.

DESCRIPTION OF PRIOR ART

Azeotropic distillation is the method of separating close boiling compounds or azeotropes from each other by carrying out the distillation in a multiplate rectification column in the presence of an added liquid, said liquid forming an azeotrope with one or both of the compounds to be separated. Its presence on each plate of the rectification column alters the relative volatility in a direction to make the separation on each plate greater and thus require either fewer plates to effect the same separation or make possible a greater degree of separation with the same number of plates. The azeotrope forming agent is introduced with the feed to a continuous column. The azeotrope forming agent and the more volatile component are taken off as overhead product and the less volatile component comes off as bottoms product. The usual methods of separating the azeotrope former from the more volatile component are cooling and phase separation or solvent extraction.

The usual method of evaluating the effectiveness of azeotropic distillation agents is the change in relative volatility of the compounds to be separated. Table 1 shows the degree of separation or purity obtainable by theoretical plates at several relative volatilities. Table 1 shows that a relative volatility of at least 1.2 is required to get an effective separation by rectification.

TABLE 1

Effect of Relative Volatility on Theoretical Stage Requirements.

| Separation Purity, Both Products (Mole Fraction) | Relative Volatility | | | | | | |
|---|---|---|---|---|---|---|---|
| | 1.02 | 1.1 | 1.2 | 1.3 | 1.4 | 1.5 | 2.0 | 3.0 |
| | Theoretical Stages at Total Reflux | | | | | | |
| 0.999 | 697 | 144 | 75 | 52 | 40 | 33 | 19 | 12 |
| 0.995 | 534 | 110 | 57 | 39 | 30 | 25 | 14 | 9 |
| 0.990 | 463 | 95 | 49 | 34 | 26 | 22 | 12 | 7 |
| 0.98 | 392 | 81 | 42 | 29 | 22 | 18 | 10 | 6 |
| 0.95 | 296 | 61 | 31 | 21 | 16 | 14 | 8 | 4 |
| 0.90 | 221 | 45 | 23 | 16 | 12 | 10 | 5 | 3 |

There are a number of commercial processes which produce complex mixtures of alcohols, e.g. the Fischer-Tropsch process which produces a series of homologous alcohols. Two of the commonest alcohols usually present are 1-butanol, B.P.=118° C. and 2-pentanol, B.P=120° C. The relative volatilty between these two is 1.08 which makes it very difficult to separate them by conventional rectification. Azeotropic distillation would be an attractive method of effecting the separation of 1-butanol from 2-pentanol if agents can be found that (1) will create a large apparent relative volatility between 1-butanol and 2-pentanol and (2) are easy to recover from the 1-butanol. Table 2 shows the relative volatility required to obtainf 99% purity. With no agent, the relative volatility is 1.08 and 160 actual plates are required. With an agent giving a relative volatility of 1.6, only 27 plates are required.

TABLE 2

Theoretical and Actual Plates Required vs. Relative Volatility for 1-butanol - 2-Pentanol Separation

| Relative Volatility | Theoretical Plates Required At Total Reflux, 99% Purity | Actual Plates Required 75% Efficiency |
|---|---|---|
| 1.08 | 120 | 160 |
| 1.3 | 35 | 47 |
| 1.6 | 20 | 27 |

OBJECTIVE OF THE INVENTION

The object of this invention is to provide a process or method of azeotropic distillation that will enhance the relative volatility of 1-butanol from 2-pentanol in their separation in a rectification column. It is a further object of this invention to identify organic compounds which in addition to the above constraints, are stable, can be separated from 1-butanol and recycled to the azeotrope column with little decomposition.

TABLE 3

Effective Azeotropic Distillation Agents For Separating 1-Butanol From 2-Pentanol

| Compounds | Relative Volatility |
|---|---|
| None | 1.08 |
| Benzene | 1.3 |
| Toluene | 1.2 |
| Hexane | 1.38* |
| 1-Hexene | 1.25 |
| Heptane | 1.3 |
| 1-Heptene | 1.3 |
| 3-Methyl pentane | 1.2 |
| 1-Octene | 1.25 |
| Cyclopentane | 1.35 |
| Cyclohexane | 1.25 |
| Methyl cyclohexane | 1.6* |
| Isopropyl acetate | 1.2 |
| 4-Methyl-2-pentanone | 1.2 |

*Data Obtained in Multiplate Rectification Column

SUMMARY OF THE INVENTION

The objects of this invention are to provide a process for separating 1-butanol from 2-pentanol which entails the use of certain organic compounds as the agent in azeotropic distillation.

DETAILED DESCRIPTION OF THE INVENTION

I have discovered that certain organic compounds will greatly improve the relative volatility of 1-butanol to 2-pentanol and permit the separation of 1-butanol from 2-pentanol by rectification when employed as the agent in azeotropic distillation. Table 3 lists the compounds that I have found to be effective. They are benzene, toluene, hexane, 1-hexene, heptane, 1-heptene, 3-methyl pentane, 1-octene, cyclopentane, cyclohexane, methyl cyclohexane, isopropyl acetate and 4-methyl-2-pentanone.

THE USEFULNESS OF THE INVENTION

The usefulness or utility of this invention can be demonstrated by referring to the data presented in Tables 2 and 3. All of the successful agents show that 1-butanol can be separated from 2-pentanol by means of azeotropic distillation in a rectification column and that the ease of separation as measured by relative volatility is considerable.

WORKING EXAMPLES

Example 1

Twenty-seven grams of 1-butanol, 13 grams of 2-pentanol and 40 grams of 1-octene were charged to a vapor-liquid equilibrium still and refluxed for 5 hours. Analysis indicated a vapor composition of 74.8% 1-butanol, 25.2% 2-pentanol; a liquid composition of 70.3% 1-butanol, 29.7% 2-pentanol. This is a relative volatility of 1.25.

Example 2

Sixty grams of 1-butanol, 40 grams of 2-pentanol and 140 grams of hexane were placed in the stillpot of a 5.6 theoretical plate glass perforated plate rectification column and refluxed for four hours. The overhead composition was 89.9% 1-butanol, 10.1% 2-pentanol; the bottoms composition was 59.2% 1-butanol, 40.8% 2-pentanol. This is a relative volatility of 1.38.

Example 3

Fifty grams of 1-butanol, 50 grams of 2-pentanol and 140 grams of methyl cyclohexane were placed in the stillpot of a 5.6 theoretical plate glass perforated plate rectification column and refluxed for four hours. The overhead composition was 96.7% 1-butanol, 3.3% 2-pentanol; the bottoms composition was 68% 1-butanol, 32% 2-pentanol. This is a relative volatility of 1.6.

I claim:

1. A method for recovering 1-butanol from a mixture of 1-butanol and 2-pentanol which comprises distilling a mixture of 1-butanol and 2-pentanol in the presence of an azeotrope forming agent, recovering the 1-butanol and the azeotrope forming agent as overhead product and obtaining the 2-pentanol as bottoms product, wherein said azeotrope forming agent consists of one material selected from the group consisting of 1-hexene, 1-heptene, 3-methylpentane, 1-octene, cyclopentane, cyclohexane and methyl cyclohexane.

* * * * *